United States Patent [19]

Gordon et al.

[11] Patent Number: 4,476,248
[45] Date of Patent: Oct. 9, 1984

[54] CRYSTALLIZATION OF IBUPROFEN

[75] Inventors: Roger E. Gordon, Portage; Sanjay I. Amin, Oshtemo Township, Kalamazoo County, both of Mich.

[73] Assignee: The Upjohn Company, Kalamazoo, Mich.

[21] Appl. No.: 517,116

[22] Filed: Jul. 25, 1983

Related U.S. Application Data

[63] Continuation-in-part of Ser. No. 470,820, Feb. 28, 1983, abandoned.

[51] Int. Cl.$^3$ ............................................. C07C 51/42
[52] U.S. Cl. .................................................... 562/494
[58] Field of Search ......................................... 562/494

[56] References Cited

U.S. PATENT DOCUMENTS 3,385,886  5/1968  Nicholson et al. ................... 560/105
4,189,596  2/1980  VanRheenen ....................... 560/105

FOREIGN PATENT DOCUMENTS 820267  1/1975  Belgium .............................. 562/494

OTHER PUBLICATIONS

Kirk–Othmer–Encyclopedia of Chem. Technology, 2nd Edit., (Supp. vol.), John Wiley & Sons, (1971), 889–910.
Derwent Abstract 38877x/21 of Japan 5 1041-338 dated Apr. 7, 1976.
Derwent Abstract 38878x/21 of Japan 5 1041-339 dated Apr. 7, 1976.

*Primary Examiner*—Paul J. Killos
*Attorney, Agent, or Firm*—John T. Reynolds

[57] ABSTRACT

Ibuprofen is crystallized from a $\delta H \geq 8$ liquid such as a $C_1$ to $C_3$-alkanol, e.g., methanol, containing solutions thereof to obtain ibuprofen crystals which are equant (cube, sphere or grain) in shape, which ibuprofen crystals have larger average partile size, higher bulk density, lower bulk volume and improved flow properties compared to previously known bulk ibuprofen crystalline materials.

17 Claims, 9 Drawing Figures

SOLUBILITY OF IBUPROFEN IN VARIOUS SOLVENTS

IBUPROFEN CRYSTALS FROM METHANOL

IBUPROFEN CRYSTALS FROM 10% WATER/90% METHANOL (v/v)

IBUPROFEN CRYSTALS FROM HEXANE

4,476,248

CRYSTALLIZATION OF IBUPROFEN

CROSS REFERENCE

The present application is a continuation-in-part of co-pending application Ser. No. 470,820, filed Feb. 28, 1983 and now abandoned.

INTRODUCTION

This invention relates to crystalline ibuprofen having better physical properties than previously known crystalline ibuprofen materials. More particularly, this invention provides an improved process for preparing crystalline ibuprofen of larger average particle size, lower bulk volume and improved flow properties, faster dissolution rate profiles, reduced sublimation rates and better compressibility properties.

BACKGROUND OF THE INVENTION

Ibuprofen is now a well-known, useful, anti-inflammatory compound which can be named chemically as 2-(4-isobutylphenyl)propionic acid. To our knowledge, ibuprofen is presently crystallized, in commercial scale processes, from commercial hexane or heptane. These aliphatic hydrocarbon solvents characteristically produce ibuprofen crystals which are rod or needle shaped. Historically, compounds which exist in the rod or needle crystal shape or habit have experienced poor flow and ibuprofen isn't any exception to this observation. Shape also seems to play a role in ibuprofen's tendency to stick to the faces of the tablet punches and dies during compressing and its tendency to laminate during decompression. In order to alleviate these undesirable manufacturing properties, the physical pharmacists must develop a formulation which will mask all of these traits. Seldom is a formulation successful in obtaining all of these goals. Therefore, pharmaceutical production and process research personnel have continued to search for chemical and physical process procedures which will improve upon the manufacturing of the currently available ibuprofen.

It was known generally about compound crystallization procedures that larger particles ($40\mu$+) had higher bulk densities. Also, it was known generally that larger particles (laths) were obtained as concentration of ibuprofen in the hexane or heptane solvent mixture magma was increased. Smaller particles ($>20\ \mu$) are obtained at lower concentrations (0.35 to 0.2 g/cm) and they are acicular/laths. However, to our knowledge, no one knew that large particle crystalline ibuprofen having higher bulk density, lower bulk volume, excellent flow properties, and different particle shape (equant and hexagonal) could be obtained by crystallization of ibuprofen, an acid, from any solvent which has a hydrogen bonding solubility parameter Index ($\delta H$) of at least 8 Hilderbrand units.

OBJECTS OF THE INVENTION

It is an object of this invention to satisfy the above desire of those in the art for an improved crystalline habit and crystal shape of ibuprofen, and to provide the art with a process for preparing crystalline ibuprofen which has larger average particle size, higher bulk denisity, lower bulk volume, and improved flow properties, compared to previously known bulk ibuprofen materials.

It is a further object of this invention to provide the art with a crystalline ibuprofen which has larger average particle size range, having excellent flow properties, and the majority of said particles having equant or hexagonal shaped crystals of low aspect ratio.

Other objects, aspects and advantages of this invention will become apparent from reading the remaining specification and the claims which follow.

SUMMARY OF THE INVENTION

Briefly, it has been found that when ibuprofen is dissolved in and crystallized from a solution thereof or containing a substantial amount of any solvent which has a hydrogen bonding parameter ($\delta H$) equal or greater than ($\geq$) 8 hilderbrand units, e.g., a $C_1$ to $C_3$-alkanol, preferably methanol, there is obtained crystalline ibuprofen having larger particle size, on average, a substantial drop in bulk volume, little, if any, static charge on the particles, faster dissolution rate properties, reduced sublimation rate, and excellent manufacturability, as compared to crystalline ibuprofen obtained by crystallizing ibuprofen from heptane or hexane or commercial forms thereof. Moreover, the above $\delta H \geq 8$ crystallized ibuprofen has excellent flow characteristics, the bulk of said ibuprofen crystals being equant (cube, sphere or grain) shape, with an average length to width aspect of about 4:1 or less, as opposed to small acicular (needle) or lath (blade) shaped crystals of ibuprofen obtained from heptane or hexane, having an average length to width aspect ratio of about 6:1 or greater.

Ibuprofen, when crystallized out of these $\delta H \geq 8$ solvents, not only achieves these goals (improved flow and reduced sticking and lamination tendencies), but also improves upon ibuprofen's particulate dissolution rate, increases its bulk density, reduces its sublimation rate and promotes better compaction or bonding properties (alleviating sticking and lamination problems). As a result of this process, a more cost effective manufacturing process can be developed by reducing pharmaceutical production down time, due to compressing problems (sticking and lamination), requiring less formulation time and handling, and eliminating energy cost required in the drying operations. In addition to cost reduction, the standard test dissolution time has been significantly reduced for a tablet dosage form from 8 minutes to 3 minutes for $T_{80}$, and the sublimation rate, which has been hypothesized to limit the product shelf-life, has been reduced by a factor of 2. Thus, using these $\delta \geq 8$ solvents, e.g., a $C_1$ to $C_3$-alkanol such as methanol in the crystallization of ibuprofen has improved its physical properties and the manufacturability of ibuprofen.

GRAPHS AND PHOTOGRAPHS

FIG. 1 is an abscissa/ordinate graph plotting solubility of ibuprofen in grams per 100 ml in a number of solvents, including hexane/heptane, ethyl acetate, isopropanol, ethanol, methanol and methanol-water mixtures against temperature, on a semilog scale, in inverse degrees Kelvin (1/T) X $10^{+3}$ (°K). *The graph shows that these* $C_1$ to $C_3$-alkanols dissolve substantially more ibuprofen therein than the hydrocarbon solvents, hexane or heptane, at a given temperature, and that solubility goies down in each solvent system as temperature decreases.

The photographs show the different crystal structure of ibuprofen obtained from methanol and methanol/water mixtures.

Figure 7:
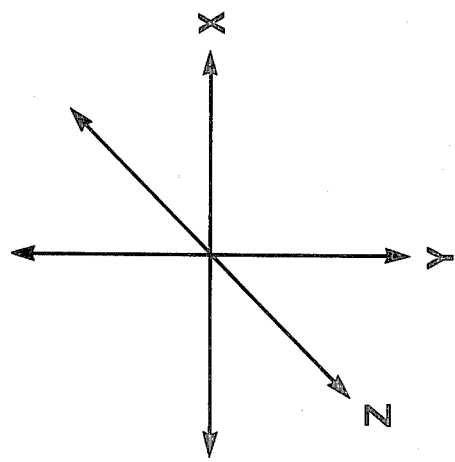

FIG. 7 represents the dimensions which should ideally be utilized in completely defining a crystal's habit: width (x-axis), thickness (y-axis), and length (z-axis). However, since only two dimensions can be accurately quantified microscopically, the simplest system of habit description involves quantifying the length to width ratio (z:x ratio) which are readily attainable microscopically.

Figure 8:
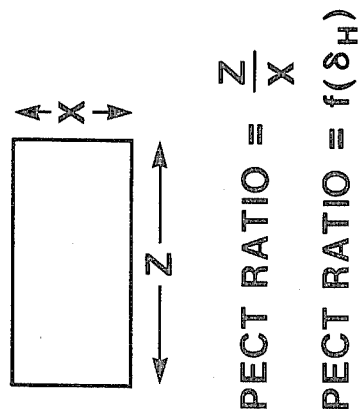

FIG. 8 illustrates the x axis was always defined as the shortest dimension of the ibuprofen crystal and the z axis the longest dimension of the ibuprofen crystal.

FIG. 8 is a rectangle defined by x (shorest dimension of the ibuprofen crystal) and z (the longest dimension of the ibuprofen crystal. The aspect ratio of the various ibuprofen crystals referred to herein is defined as Aspect Ratio = z (longest dimension) ÷ x (shortest dimension)

The aspect ratio of the ibuprofen crystals is a function of the hydrogen bonding property or parameter ($\delta H$) of the solvent system used.

Figure 9:
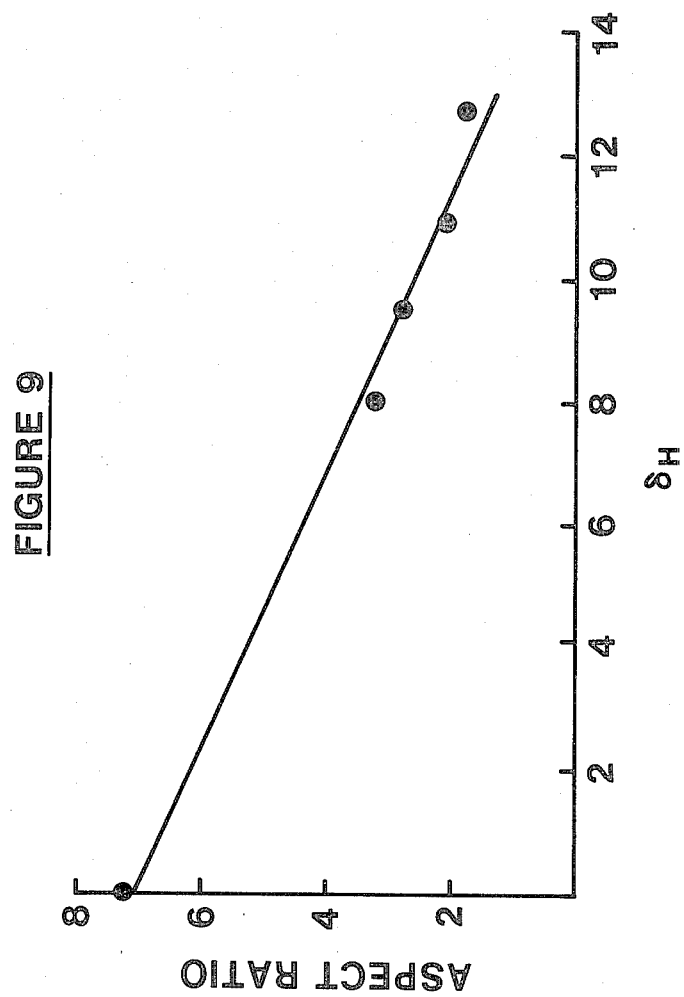

FIG. 9 is an ordinate/abscissa graph plotting aspect ratio (ordinate/vertical coordinate) against the hydrogen bonding parameter ($\delta H$) of the solvent system used. The ball-type points on the graph, from left to right depict the aspect ratios of ibuprofen crystallized out of hexane, isopropyl alcohol (isopropanol), ethanol, methanol and ethylene glycol, respectively.

We have found that the herein described and claimed crystal forms of ibuprofen are obtained when the solvent or solvent mixtures used have a hydrogen bonding parameter ($\delta H$) having at least about 8 Hildebrand units, preferably greater than 9 Hildebrand units. We have found that to obtain this desired crystal habit form of ibuprofen, the most practical solvents to accomplish this crystal habit form are those which are $C_1$ to $C_3$-alkanols per se, or are liquid mixtures containing at least about 10 percent by volume of the $C_1$ to $C_3$-alkanols.

For an article discussing polarity ($\delta P$) hydrogen bonding ($\delta H$) and dipole moment ($\delta D$) parameters of various solvents in mathematical terms, see "SOLUBILITY PARAMETERS" in Kirk-Othmer—*ENCYCLOPEDIA OF CHEMICAL TECHNOLOGY*, 2nd Ed., Supplemental Volume, pp. 889-910, by John Hansen et al., published by John Wiley & Sons (1971).

The dipole moment component parameter ($\delta D$) of these solvents was not considered critical or did not significantly influence the choice of solvent or solvent mixtures for ibuprofen solution and crystallization so they are not shown on the graphs. We have more recently found that polarity parameter ($\delta p$) of the solvent or solvent system is also of little influence in determining ibuprofen crystal habit.

DETAILED DESCRIPTION OF THE INVENTION

It has been found, according to this invention, that an improved crystalline habit of ibuprofen can be obtained by crystallizing ibuprofen from a solution of ibuprofen in or containing an influential amount of an ibuprofen liquid solvent which has a hydrogen bonding solubility parameter ($\delta H$) of at least 8, expressed herein as ($\delta H \geq 8$), e.g., a $C_1$ to $C_3$-alkanol. The $C_1$ to $C_3$-alkanols include methanol, ethanol, n-propanol and isopropanol, and mixtures thereof. Methanol is preferred.

Ibuprofen has not been crystallized out of pure water alone by the herein described process to any substanial extent due to the very low solubility of ibuprofen and hence its very slow crystal growth rate in pure water. However, in ibuprofen manufacturing processes ibuprofen is crystallized from its reaction mixtures by precipitating it from an aqueous solution of the sodium ibuprofen salt, for example, by addition to that salt solution of an inorganic acid to the aqeous sodium ibuprofen solution, or from aqueous/heptane or aqueous/methylene chloride mixture, as known in the art. The ibuprofen crystals so obtained are such that the ibuprofen crystal aspect ratio averages greater then (>) 6. In contrast, here, according to this invention, we have discovered how to obtain ibuprofen crystals having a crystal aspect ratio averaging no greater than about 4, for example, (after ibuprofen has been manufactured as above) by dissolving ibuprofen per se in the herein defined solvent media, without any substantial salt formation, and crystallizing the ibuprofen therefrom, as described herein to obtain described, significantly improved crystal habit ibuprofen.

Examples of other liquid and liquid mixture solvents for ibuprofen which will give the desired low aspect ratio ibuprofen crystal habit include ethylene glycol, methanol/water and ethanol/water mixtures containing at least about 10 v/v percent of the methanol or ethanol respectively, ethanolamine, ethylene, diamine, formamide, succinic anhydride, ethylene cyanohydrin, allyl alcohol, 1-propanol, 2-propanol, formic acid, 1,3-benzenediol, water glycerol, propylene glycol, 1,3-butamediol, diethylene glycol, triethylene glycol, hexylene glycol, dipropylene glycol, and the like.

The crystalline ibuprofen having the above-mentioned improved physical properties can be prepared by crystallizing or precipitating the ibuprofen from one or more of the above solvents by a numer of methods. Our method can be described by the following sequence of steps:

forming a solution of ibuprofen in the selected $\delta H \geq 8$ solvent or solvent mixture at a temperature of from about 20° to 60° C.;

adjusting the temperature of the ibuprofen/solvent solution as necessary to above the saturation point to effect essentially complete solution of the ibuprofen content therein, cooling the resulting ibuprofen in solvent solution to a temperature below the saturation point for theat ibuprofen/solvent solution to obtain a state of supersaturation of ibuprofen in the $\delta H \geq 8$ solvent containing solution thereof, cooling the resulting supersaturated ibuprofen in solution over about 0.5 to about 3 hours to 0° to −20° C. to effect crystallization and precipitation of ibuprofen from the solution thereof, agitating the cooled ibuprofen/$\delta H \geq 8$ solvent mixture for a time sufficient to obtain solid/liquid equilibrium in the mixture, and separating the crystalline ibuprofen from the liquid component of the mixture.

The crystallization of ibuprofen from its $\delta H \geq 8$ solvent, e.g., a $C_1$ to $C_3$-alkanol containing solvent can be accomplished by cooling the solution, with or without seeding the solution. However, we prefer to seed the ibuprofen/$\delta H \geq 8$ solvent containing solution with ground or unground ibuprofen to induce secondary nucleation during the cooling period. The solid form ibuprofen seed can be ground, e.g., to an average particle size of about 10 to 20 microns.

Alternatively, or in conjunction with seeding, the new desired ibuprofen can be crystallized in the desired crystal habit from the $\delta H \geq 8$ solvent containing solution thereof by mixing therewith a liquid which reduces the solubility of ibuprofen in the resulting ibuprofen/$\delta H \geq 8$ solvent/liquid mixture. The additional diluent liquid or cosolvent used with the $\delta H \geq 8$ solvent comprises one or more liquids, the composite or result of which additional liquid or liquids is to effect a $\delta H \geq 8$ solvent diluent which is less polar and which has less hydrogen bonding capacity and a lower solubility parameter for ibuprofen than the pure $\delta H \geq 8$ solvent component.

A simple mixture of choice is to use a $C_1$ to $C_3$-alkanol/water mixture containing up to about 90 percent water, by volume, in the solvent mixture. Methanol is the preferred $\delta H \geq 8$ solvent for these water/$C_1$ to $C_3$-alkanol solvent mixtures.

Examples of preferred additional liquids for use in admixture with the $C_1$ to $C_3$-alkanol would be water and liquid alkane and aromatic hydrocarbons, esters, glycols, trihydric alcohols, such as pentane, hexane, heptane, ethyl acetate, benzene, toluene, xylene, ethylene glycol, propylene glycol, glycerine or other solvent systems which have lower hydrogen bonding properties and lower ibuprofen solubility property than methanol. The solvent mixtures used herein can contain up to about 90 percent by volume of non-$\delta H \geq 8$ solvent liquid, that is, the ibuprofen solvent system contains at least about 10 percent (v/v) of the liquid solvent which has the $\delta H \geq 8$ properties, e.g., $C_1$ to $C_3$-alkanol, preferably methanol. The ibuprofen-solvent system can also be a simple water/$C_1$ to $C_3$-alkanol (up to 90 prcent v/v water) mixture, preferably a water/methanol mixture to obtain ibuprofen crystals therefrom in an equant crystal habit.

We have also found that crystalline ibuprofen of the desired larger bulk density can also be obtained from liquid mixture solutions of ibuprofen which contain the $\delta H \geq 8$ solvent as a principal solvent component therein. For example, mixtures of solvents for ibuprofen such as hexane, heptane, ethyl acetate with $C_1$ to $C_3$-alkanols, present in at least ten percent by volume, based on the volume of the non-$C_1$ to $C_3$-alkanol solvent, can be used to obtain crystalline ibuprofen having the improved crystalline habit, obtainable with the $C_1$ to $C_3$-alkanol as the only solvent. We have obtained crystalline ibuprofen having the new crystalline habit of this invention from solutions of ibuprofen in 50:50 (v/v) mixutes of heptane and methanol. It appears that it is only necessary to have sufficient $\delta H \geq 8$ solvent present in the solution mixture to influence or induce the formation of the new, more desirable ibuprofen crystal habit.

Another commonly used method of crystallization which could be used to crystallize ibuprofen in the desired crystal habit would be to dissolve the ibuprofen in the $\delta H \geq 8$ solvent and either add this ibuprofen/$\delta H \geq 8$ solvent solution to a mother solvent liquid in which ibuprofen has a lower solubility, e.g., add an ibuprofen/$C_1$ to $C_3$-alkanol solution to water, or to a liquid alkane such as hexane or heptane, or mixtures thereof. The reverse addition procedure could also be used. That is, the lower ibuprofen solubility liquid, e.g., water, hexane, heptane, or the like, could be added to the ibuprofen/$\delta H \geq 8$ solvent solution to initiate and effect ibuprofen crystallization. This method is commonly referred to as precipitation. When ibuprofen is precipitated by adding a solution of ibuprofen in the $\delta H \geq 8$ solvent to either water or a liquid alkane, the ibuprofen crystals so obtained share better flow characteristics than does ibuprofen crystallized from a liquid alkane such as hexane or heptane alone.

We have discovered that if the Hildebrand hydrogen bonding parameter ($\delta H$) of the solvent system used for dissolving the ibuprofen therein and crystallizing ibuprofen therefrom is above or equal to 8 Hildebrand units (Ref.: *ENCYCLOPEDIA OF CHEMICAL TECHNOLOGY*, Kirk-Othmer, 2nd Ed., (1971) Supplement Volume, pp. 889–910) the ibuprofen crystal habit obtained from that system will have the improved crystal structure defined herein. This desired ibuprofen crystal habit is more assured if the hydrogen bonding component of the solubility parameter of the solvent system used is 9 or greater Hildebrand units before crystallization begins. We have discovered that the easiest, practical way to obtain these ibuprofen-solvent properties is to use at least about 10 percent v/v $C_1$ to $C_3$-alkanol, preferably methanol, in the solvent system for ibuprofen.

Average crystal size of ibuprofen can be altered via adjustment of a number of vaiables, e.g., by changing the mixing rate, the temperature of crystallization, the concentration of ibuprofen in the $\delta H \geq 8$ solvent and the amount of liquid medium with which the iburpofen/$\delta H \geq 8$ solvent mixture is mixed. These parameters have not been completely explored or optimized since we prefer to use a simple, single solvent or solvent mixture in a plant process from the point of view of simplifying the recovery of solvent from the filtrate for reuse in the process. The use of the mixed solvents procedure, by precipitation technique, as mentioned hereinabove, would necessitate the need for separation as by fractional distillation of solvents, e.g., water/$C_1$ to $C_3$-alkanol, hexane/$C_1$ to $C_3$-alkanol, heptane/$C_1$ to $C_3$-alkanol, etc., which mixtures are obtained as filtrates after removing the bulk of the crystallized ibuprofen therefrom, and would consume more energy than is desired. However, for the purposes of obtaining ibuprofen of the desired crystal habit here, either the seeding method or solvent mixing method can be used to initiate crystallization of ibuprofen from the $\delta H \geq 8$ solvent system, depending upon the overall economics to be gained by either method.

In preparing the solutions of ibuprofen in the $\delta H \geq 8$ solvent, e.g., $C_1$ to $C_3$-alkanol, care should be taken to dissolve sufficient ibuprofen therein to be efficient in operation and effective to obtain the desired crystal habit of ibuprofen therefrom upon cooling. However, too much ibuprofen should not be dissolved in the $\delta H \geq 8$ solvent so as to cause spontaneous nucleation and/or thick slurries so as to plug containers, pipelines and valves, or to form a crystalline ibuprofen slurry so thick as to be difficult to handle in plant scale equipment when the solution is cooled. Using methanol as an exemplary single solvent the ibuprofen/methanol solution becomes saturated at about 40°–45° C. when about 220 g of ibuprofen have been dissolved in 100 ml of methanol. This is a practical, efficient and effective amount of ibuprofen in methanol to work with as the solution is cooled to the desired final crystallization and equilibrium temperature, here, to about 0° C. for a practical recovery or yield of ibuprofen crystals of the desired new crystal habit. The ibuprofen/$C_1$ to $C_3$-alkanol solution as it is cooled should have a fluidity such that it can be handled in normal plant processing equipment. We have found that if there is dissolved a larger than optimum amount of ibuprofen than that which can be dissolved in methanol at about 40° to 45° C., e.g., by saturating the $C_1$ to $C_3$-alkanol with ibuprofen at, say, 50° to 98° C., then upon cooling this solution to final crystallization and equilibrium temperature, say, to about 0° C., there is formed a very thick slurry of ibuprofen crystals in the solvent mixture, which slurry mixture is very difficult to handle in a normal batch-type fine chemical plant operation.

We prefer to use the ibuprofen seeding procedure to initiate the controlled type of ibuprofen crystallization of the desired crystal habit. We prefer to avoid the unseeded primary or spontaneous nucleation type of ibuprofen crystallization, which occurs at about 20° to 30° C. Such primary nucleation is difficult to control, produces ibuprofen crystals which are smaller on average than is obtained using seeding procedures, and gives crystalline ibuprofen which has somewhat poorer flow characteristics upon handling, but such crystals are still better than crystalline ibuprofen obtained by crystallizing ibuprofen from hexane or heptane along. For some circumstances, it may be desirable to make smaller average particle size ibuprofen, e.g., for enhanced bioavailability and better blood levels over time. In such cases, smaller ibuprofen particles with good flow properties, made according to this invention, would be preferable to ibuprofen crystallized from alkane hydrocarbon solvents since the flow and handling characteristics are better due to the non-acicular or non-lath shaped crystalline ibuprofen obtained according to this invention. Normally, however, we prefer to use the seeding with ground ibuprofen procedure to induce crystallization of ibuprofen from a supersaturated $C_1$ to $C_3$-alkanol solution of ibuprofen, as indicated above, to obtain more secondary nucleation. The seeded solution can be agitated or stirred between zero and sixty minutes to promote crystal growth and efficient mass transfer from the solution to the crystal face.

Figure 1:
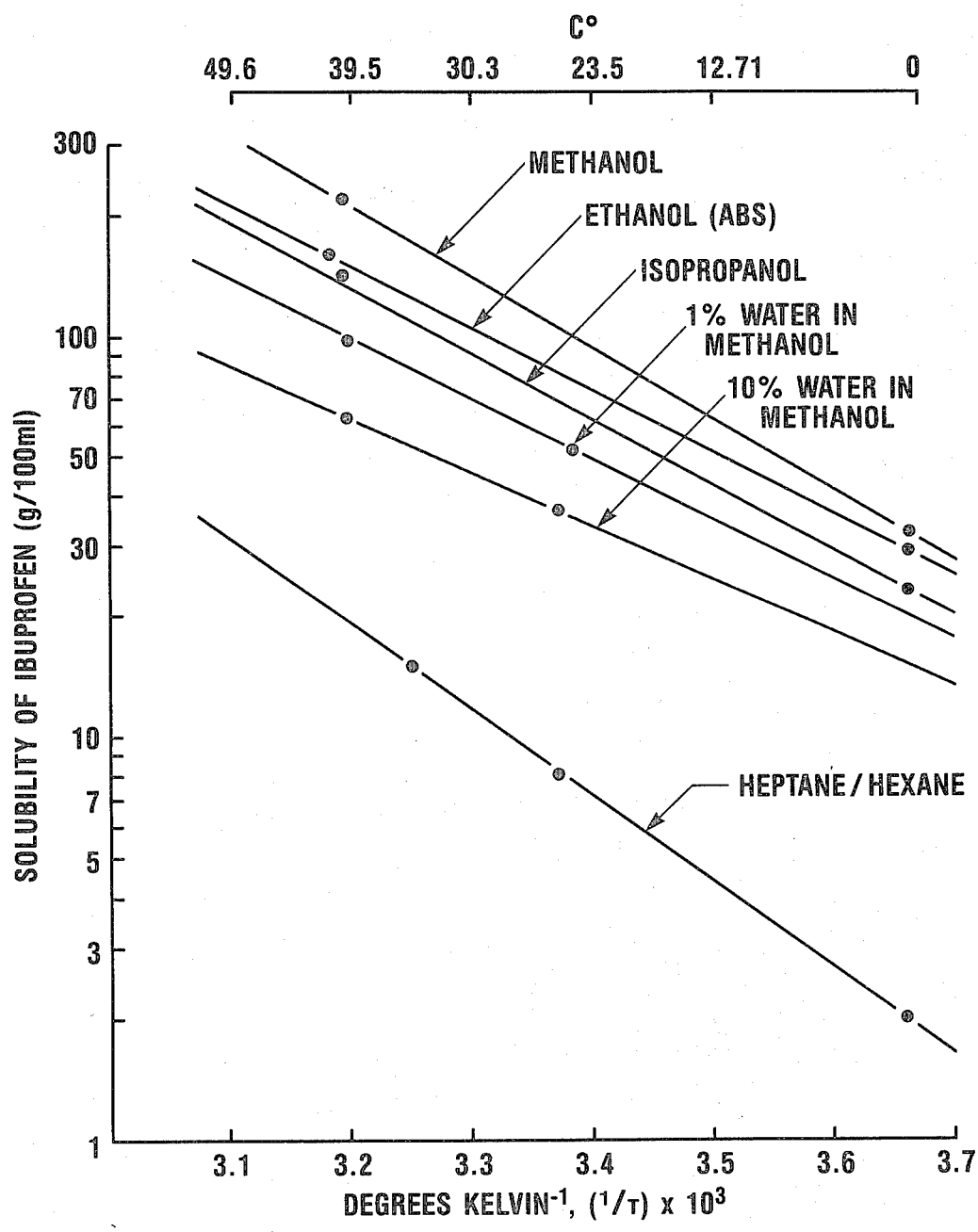
Figure 2:
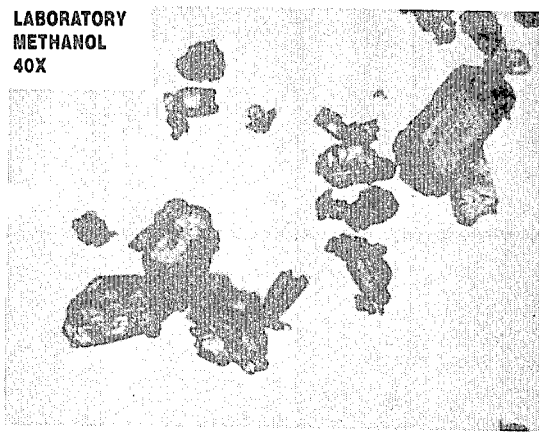
FIGS. 2, 3 and 4 are photographic exhibits of ibuprofen crystals from methanol solution made in the laboratory and pilot plant according to this invention.
Figure 3:
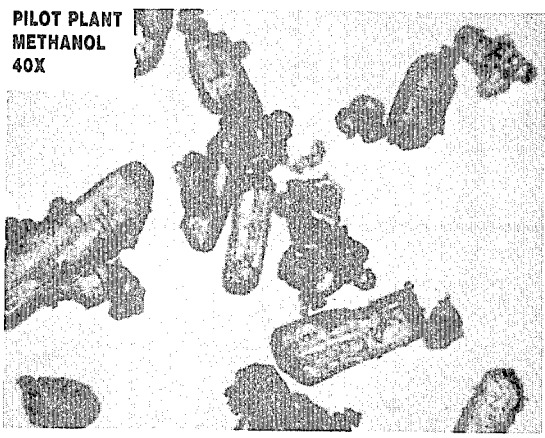
Figure 4:
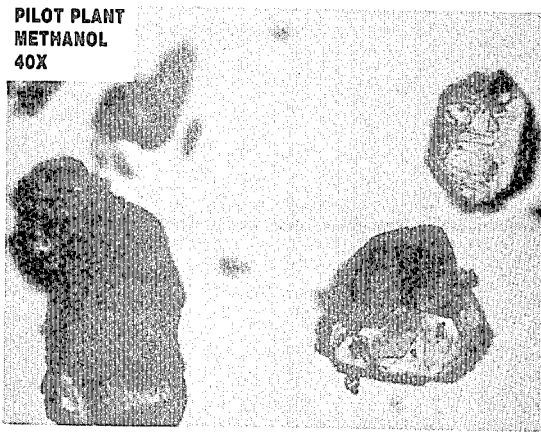
Figure 5:
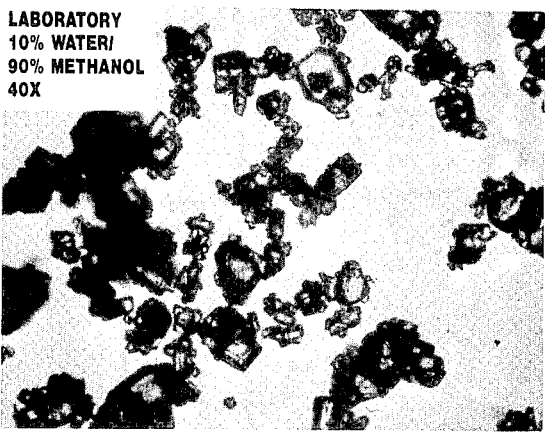
FIG. 5 is a photographic exhibit which shows the effect of adding water to methanol and use of this mixture as a crystal salts in solvent.
Figure 6:
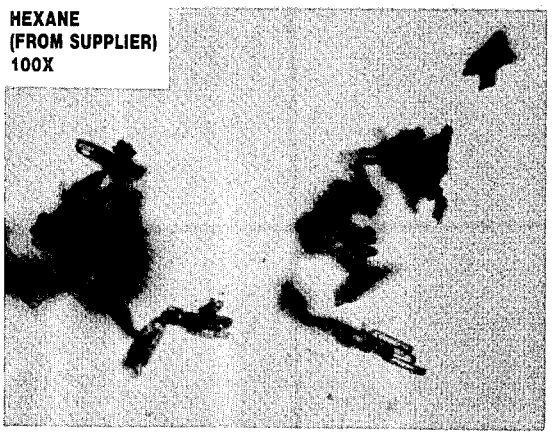
FIG. 6 is a photographic exhibit of crystalline ibuprofen from commercial hexane, as received from a supplier.

Thus, we have found that crystallization of ibuprofen from these $\delta H \geq 8$ solvent, particularly from methanol, by way of seeding or by formation of ibuprofen in mixtures of a $\delta H \geq 8$ solvent with other liquids such as alkanols, water, $C_5$ to $C_9$-alkanes, and the like, results in ibuprofen having a crystal habit which is a significant improvement and advantageous over hexane or heptane crystallized ibuprofen in terms of pharmaceutical processing, e.g., in improving the manufacturability and handling of ibuprofen, such is evidenced by faster dissolution rates, reduced sublimation characteristics of the ibuprofen material and better acceptance in direct compaction tablet formulation operations. Moreover, the equant ibuprofen crystal habit (FIGS. 2, 3, 4 and 5), which is non-acicular and non-lath type, illustrated by FIG. 6, is believed to be new and has not been seen before with ibuprofen from any source of manufacture, to our knowledge.

More recently, several lots of ibuprofen were recrystallized from 10 percent v/v water in ethanol. The advantage of this water/ethanol solvent system over ethanol is a reduction in particle size and narrow crystal size distribution with minimal loss in the flow characteristics of the improved crystal form of ibuprofen of this invention. Reproducibility was good for ibuprofen lot sizes of 1.6 kilograms. However, in terms of flow properties for phamaceutical composition use, ibuprofen crystallized from a methanol containing solvent still is the solvent system of choice. Also, data now available indicates that ibuprofen crystallized from methanol gives essentially the same bioavailability as does ibuprofen crystallized from hexane/heptane, the prior known solvent.

It is well known in the literature that a change in solvent can change the crystal habit of a chemical compound. However, there are no known means of predicting which solvent would result in a given, desirable crystal habit. Desirable crystal habits of chemical compounds are still learned only by experimental trial and error manifestations.

The invention is further exemplified by the following detailed examples, which are not intended to limit the scope of the invention.

EXAMPLE 1

Crystallizing Ibuprofen From Methanol

In a 1000 ml round bottomed flask there was charged 100 ml of industrial grade methanol. Then 94.93 g of bulk ibuprofen USP was added to the methanol to obtain a saturated solution. The resulting methanol/ibuprofen solution was heated to 40° C. Then another 123.78 g of ibuprofen was added to obtain saturation of the solution at that temperature. Thus a total of 218.71 g of ibuprofen had been added at 40° C. The resulting solution was heated to 45° C. to ensure dissolution of all the ibuprofen present and then the resulting ibuprofen in methanol solution was cooled to 40° C. and seeded with 0.1 of ground ibuprofen to induce crystallization. Since crystallization did not proceed, the mixture was further cooled to 36° C. and re-seeded with another 0.1 g of ibuprofen. The mixture was stirred for 30 minutes at 36° C. (to promote crystal growth) and then cooled to 0° C. over 2 hours. The resulting slurry mixture was stirred at 0° C. for 2 hours and then filtered over a precooled 600 ml coarse sized filter. The net weight of ibuprofen crystalline solid material obtained was 168.9 g, leaving 33.39 g of ibuprofen still in the filtrate. The recovery could have been increased if the temperature had been lowered to −10° to −15° C.

The crystalline ibuprofen was dried overnight with nitrogen. Since the crystalline ibuprofen was not completely dried, it was further dried in a vacuum oven for 2.5 hours at 60° C. The crystalline filtered cake was clear. The geometric volume mean diameter (GVM) of this crystalline ibuprofen was 25 microns ($\mu$). The bulk volume of this crystalline, ibuprofen before tapping was 112 ml/60 g; after tapping, the bulk volume was 96 ml/60 g. Also, 79.2 percent of this crystalline ibuprofen was retained on a 200 mesh screen and 6.2 percent was retained on a 325 mesh screen. A melt solvate test on a sample of this crystalline ibuprofen showed that no solvent (methanol) was present in this crystalline ibuprofen.

EXAMPLE 2

Methanol Crystallization With Filtrate Wash

A. Into 100 ml of industrial grade methanol there was added 218.71 g of bulk ibuprofen, obtained from a supplier. The mixture was heated to 49° C. All the ibuprofen was then dissolved into solution. The resulting ibuprofen in methanol solution was cooled to 40° C., seeded with 0.1 g of ground ibuprofen and stirred at 40° C. for 30 minutes. The resulting mixture was coolded from 40° C. to 0° C. over 2 hours. A slurry of precipitating, crystalline ibuprofen developed as cooling proceeded, such that at 14° C. there was fair agitation of the mixture and at 0° C. there was poor agitation of the mixture. The mixture was stirred at 0° C. for 2 hours.

B. In a companion run of the same dissolution/recrystallization process another 218.71 g portion of bulk ibuprofen, obtained from a supplier, was mixed and dissolved in 100 ml of methanol, when warmed to 49° C. The resulting solution was cooled to 40° C., as above, and seeded with 0.1 g of ground ibuprofen and cooled to 0° C. over 2.5 hours and then stirred at 0° C. for 2 hours before filtering the resulting slurry of crystalline ibuprofen.

In the two runs, A and B, the filtered net weights were A=185.29 g; B=185.47 g.

The batch A crystalline ibuprofen was dried at 60° C. in a vacuum oven for 2 hours. Batch B crystalline ibuprofen was dried under a nitrogen flow atmosphere overnight.

The physical, particle size properties of the two btches were as follows:

|  | A | B |
|---|---|---|
| % retained on 200/325 mesh by wet sieve analysis | 92.6/0.6% | 69.4/7.0% |
| Bulk Volume: (ml/60 g) | | |
| before tapping | 108 | 120 |
| after tapping | 92 | 96 |
| Particle Size: | | |
| geometric volume mean | 47.4μ | 48.1μ |

EXAMPLE 3

Crystallizing Ibuprofen From Isopropanol and Ethanol

A. To 100 ml of isopropyl alcohol there was added 100 g of bulk ibuprofen, from a supplier. Ibuprofen was added until the resulting solution became saturated at 34° C. The solution was saturated at 40° C. The total ibuprofen content was 140 g. The solution was heated to 45° C. and then cooled to 35° C. The ibuprofen in isopropanol solution was seeded with 0.1 g of ground ibuprofen at 38° C., stirred for 30 minutes at 37° C. and cooled from 37° C. to 0° C. over 2 hours. The mixture was stirred at 0° C. for 2 hours, filtered, and washed one with filtrate.

B. In a companion run, another 160 g of bulk ibuprofen, from the supplier, was added to 100 ml of ethanol. The solution was saturated at 41° C. Ibuprofen was warmed to 45° C. Then this mixture was heated to 45° C. and cooled to 38° C., seeded with 0.1 g of ground ibuprofen and cooled to 0° C. over 2 hours, stirred at 0° C. for 2 hours, filtered, and washed once with filtrate, as above.

The yields of crystalline ibuprofen from each run were:

| A. | 114.73 g filter cake | B. | 129.68 g filter cake |
|---|---|---|---|
|  | In flask - 1.5 g |  | 1.2 g |
|  | In mother liquors 23.52 g |  | 29.09 g |

Batch A was dried for 1 hour at 60° C. in a vacuum oven.

Batch B was dried by a flowing nitrogen atmosphere overnight.

The physical properties were as follows:

|  | A | B |
|---|---|---|
| Mesh Analyses, % retained on 200/325 Mesh | 43.8%/15.2% | 77.4%/3.0% |
| Particle Size (geometric volume mean) | 37.3μ | 37.7μ |
| Bulk Volume, (ml/60 g) | | |
| before tapping | 148 | 124 |
| after tapping | 104 | 100 |

EXAMPLE 4

Folliwing the procedure of Example 1, three 30 kg size pilot runs were made to recrystallize ibuprofen USP from methanol. The runs produced crystalline ibuprofen which was similar to laboratory runs. Data summarized below compares bulk volumes, before and after tapping, particle size and flow characteristics, with bulk crystalline ibuprofen materials obtained from different supplier thereof.

| Lot No. | Bulk Volume Before & After Tapping (ml/60 g) | Particle Size*, GVM, Microns | Flow Characteristics |
|---|---|---|---|
| In-House #1 | 104/92 | 82.6+ | Excellent |
| In-House #2 | 112/92 | 46.5 | Very Good |
| In-House #3 | 116/92 | No data | — |
| In-House #4 | 110/92 | 18.0 | Excellent |
| Supplier #1 | about 190/130 | about 20 | Poor |
| Potential Supplier #2 | 134/97 | 47.5 | Good |

The first pilot lot #1, above, with the largest average particle size, was mixed in a powder formulation. Commercially available ibuprofen was likewise mixed in a separate formulation of the same ingredients. Both powder mixes were compressed using the same load for a given constant time. The resulting compressed powder compacts were subjected to the USP dissolution test for ibuprofen. The methanol crystallized ibuprofen tablets yielded an average dissolution time for 80% of the labeled dose to be in solution of 3 minutes while the commercially available ibuprofen tablets yielded an average dissolution time for 80% of the labeled dose to be in solution of 8 minutes.

EXAMPLE 5

A saturated solution of ibuprofen was obtained in methanol at room temperature. This saturated solution container was placed in a refrigerator (about 4° C.) for 72 hours during which time the ibuprofen therein crystallized out. The ibuprofen crystals were then collected by filtration. The filtered ibuprofen crystals were vacuum dried at 40° C. and 25 mm Hg vacuum pressure for 24 hours. The dried ibuprofen crystals were passed through a 20 mesh screen, only to break up any large agglimerates of crystalline material. The crystal size and shape was not essentially disturbed because the crystalline sizes were small enough to pass through the 20 mesh screen without crystalline particle size reduction. The crystall habit of this material was equart with an average GVM (Geometric Volume Mean) particle size of 18). On further evaluation of the existing data, a direct relationship was observed between crystal habit of ibuprofen and δH of the crystallization solvent or solvents. However, before this relationship is explored, a description and definition of the terms used should be explained.

MORPHOLOGICAL CRITERIA AND DETERMINATION

The shape, habit or morphology of a crystalline material is defined by a three dimensional array in space and can exist in an infinite variety of combinations. This infinite variety of combinations in crystal habit is the primary cause of subjectivity in habit description. All habits can, however, be described as vector points on an x-y-z lattice, FIG. 7. Therefore, a statement of morphology of a crystalline substance should provide a description of the length of each axis. Since a three dimensional description cannot be obtained microscopically, the simplest system of habit description involves providing lengths of the x and z axis. This length description, or quantification, of the crystal habit is generally referred to as the aspect ration. The aspect ratio can then be defined as the crystal's length to width ratio (FIG. 8). Length in this case was interpreted to be the longest crystallographic axis (z) while width was the dimension obtained when a 90° angle to the length axis was imaged (x).

A scanning electron microscope was utilized under identical conditions and magnification to obtain the aspect ratio for ibuprofen lots crystallized out of methanol, ethanol, ethylene glycol, isopropyl alcohol, and hexane. When the average aspect ratio of these lots is plotted against the crystallization solvents' δH, a linear relationship exists (FIG. 9).

We claim:

1. Ibuprofen crystallized from a saturated solution of ibuprofen in a liquid mixture containing at least about 10 percent by volume of solvent which has a hydrogen bonding parameter (δH) equal to or greater than 8 Hildebrand units.

2. Crystallized ibuprofen according to claim 1 where the δH≧8 solvent is a $C_1$ to $C_3$-alkanol.

3. Crystallized ibuprofen according to claim 2 wherein the δH≧8 solvent is methanol.

4. A process for preparing cyrstalline ibuprofen which comprises:
   forming a solution of ibuprofen in a liquid solvent containing at least about 10 percent by volume of a δH≧8 liquid solvent at a temperature of from about 20° to 60° C.;
   adjusting the temperature of the ibuprofen: δH≧8 solvent solution as necessary to above the saturation point to effect essentially complete solution of the ibuprofen content therein;
   cooling the resulting ibuprofen in the δH≧8 solvent solution over about 0.5 to about 3 hours to 0° to −20° C. to effect crystallization and precipitation of ibuprofen from the solution thereof;
   agitating the cooled ibuprofen: δH≧8 solvent mixture for a time sufficient to obtain solid/liquid equilibrium in the mixture, and
   separating the crystalline ibuprofen from the liquid component of the mixture.

5. a process according to claim 4 wherein the supersaturated solution of ibuprofen in the δH≧8 liquid mixture is seeded with solid ibuprofen to induce crystallization during the cooling operation which follows.

6. A process according to claim 4 wherein the δH≧8 solvent component is selected from the group consisting of methanol, ethanol, isopropanol and mixtures thereof.

7. A process according to claim 5 which further includes the steps of mixing a liquid which reduces the solubility of ibuprofen in the resulting ibuprofen/δH≧8 solvent liquid mixture to effect crystallization and precipitation of ibuprofen from the resulting mixture.

8. A process according to claim 7 where the solubility reducing liquid mixed with the ibuprofen/δH≧8 liquid is selected from the group consisting of water, hexane, heptane, toluene, ethylacetate, ethylene glcyol, propylene glycol, glycerine and mixtures thereof.

9. Crystalline ibuprofen whose crystal habit is characterized as essentially equant, or hexagonal in shape.

10. A process according to claim 4 wherein the ibuprofen to be crystallized is contained in a liquid solvent mixture of a δH≧8 sovent component and a non-δH≧8 solvent liquid component, and wherein the non-δH≧8 solvent liquid component is less polar and which has less hydrogen bonding capacity for ibuprofen than a $C_1$ to $C_3$-alkanol.

11. A process according to claim 10 wherein the δH≧8 solvent liquid component is a $C_1$ to $C_3$-alkanol.

12. A process according to claim 4 wherein the ibuprofen to be crystallized is a δH≧8 solvent liquid/water mixture containing up to 90 percent water of the solvent liquid mixture.

13. A process according to claim 12 wherein the δH≧8 solvent liquid component is a $C_1$ to $C_3$-alkanol.

14. A process for preparing ibuprofen having a crystal habit which is essentially equant or hexagonal in shape which comprises crystallizing ibuprofen from a solution thereof in a liquid solvent having a hydrogen bonding parameter (δH) greater than about 8 Hildebrand units.

15. A process according to claim 4 wherein the ibuprofen is crystallized from a solvent mixture comprising about 10 percent water in ethanol, by volume.

16. Ibuprofen crystallized from a water/ethanol mixture according to claim 15.

17. Crystalline ibuprofen whose crystal habit is characterized as essentially equant in shape and an average particle size larger than 18μ and having a length to width crystal aspect ratio of 4:1 or less.

* * * * *